US00PP13981P29

(12) United States Plant Patent
Hanes

(10) Patent No.: US PP13,981 P2
(45) Date of Patent: Jul. 15, 2003

(54) VERBENA PLANT NAMED 'LAN SCARL'

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/058,039

(22) Filed: Jan. 29, 2002

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Annette H. Para
(74) *Attorney, Agent, or Firm*—Jondle & Associates PC

(57) ABSTRACT

A verbena cultivar particularly distinguished by red colored flowers, vigorous growth and semi-trailing habit.

1 Drawing Sheet

Genus and species: Verbena hybrida.
Variety Denomination: 'Lan Scarl'.

BACKGROUND OF THE NEW PLANT

The present invention comprises a new and distinct cultivar of verbena, botanically known as Verbena hybrida, and hereinafter referred to by the cultivar name 'Lan Scarl'. The new cultivar is asexually reproduced from vegetative cuttings and tissue culture resulting from the cross of the seed/pod parent 97-428-6, an unnamed and unpatented red proprietary line and the pollen parent Temari Red (PPAF), a commercial line.

'Lan Scarl' is a product of a planned breeding program intended to create new verbena cultivars with red colored flowers, dark green foliage, vigorous growth and semi-trailing habit.

The new cultivar was created in 1999 in Gilroy, Calif. and has been asexually reproduced repeatedly by vegetative cuttings and tissue culture in Gilroy, Calif. over a two year period. It has also been trialed at Gilroy, Calif.; Alberta, Canada, Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The drawing shows overall plant habit and the mature inflorescence.

DESCRIPTION OF THE NEW CULTIVAR

The following detailed descriptions set forth the distinctive characteristics of 'Lan Scarl'. The data which defines these characteristics were collected from asexual reproductions carried out in Alberta Canada. The plant history was taken on 11 week old plants grown in 4 inch pots, blossomed under natural light in a greenhouse and color readings were taken in the greenhouse in Alberta Canada. Color references are primarily to The R.H.S. Colour Chart of The Royal Horticultural Society of London (R.H.S.).

THE PLANT

Classification:
*Botanical.*—Verbena hybrida.
*Commercial.*—Verbena.
Form: Low trailing annual, decumbent.
Growth and branching habit: Vigorous growing, moderate basal branching; low trailing habit.
Height: From soil level to top of blooms: Approximately 8 cm.
Width: Approximately 75 cm.
Time to produce a finished flowering plant: 10 weeks.
Outdoor plant performance: Typical bedding plant culture, full sun in the garden, hanging baskets or container plants.
Time to initiate roots: Approximately 4 days in the greenhouse.
Time to develop roots: Approximately 7 days in the greenhouse.
Root description: Fibrous, fleshy, white.

THE LEAVES

Length: 3.5–4.1 cm.
Width: 2.5–3.1 cm.
Leaf blade shape: Ovate/broadly ovate.
Leaf margin: Irregular, crenately incised with secondary sharp teeth.
Apex aspect: Obtuse or sharp.
Base aspect: Truncate.
Foliage color: Upper surface — Yellow-green RHS 147A; Lower surface is yellow-green RHS 147B.
Texture: Moderately hairy.
Venation: Pinnatifid, pubescent.
Venation color: Upper surface is yellow-green RHS 147C; lower surface is yellow-green RHS 147C.
Petiole length: 7.5 mm.
Petiole diameter: 1.5 mm.
Petiole color: Upper surface is yellow-green RHS 147C; lower surface is yellow-green RHS 144C.

THE STEM

Length: 25–50 cm.
Diameter: 2.0–3.0 mm.

Internode length: 3.0–4.2 cm.
Color: Upper surface is yellow-green RHS 144A; lower surface is yellow-green RHS 144B.
Texture: Moderately hairy.
Anthocyanin: Moderate anthocyanin on stem, with stronger intensity along stem edge.

THE BUD

Shape: Linear.
Diameter: 2–3 mm.
Length: 14–16 mm.
Color at tight bud: Red RHS 45D.

THE FLOWER

Blooming habit: Continuous throughout the growing season.
Inflorescence type: Spike.
Spikes per plant: 7–14.
Spike depth: Approximately 5.6 cm.
Spike diameter: 6.0 cm.
Peduncle length: 3.0–5.8 cm.
Peduncle diameter: 2 mm.
Peduncle color: Yellow-green RHS 144A.
Peduncle texture: Moderately pubescent.
Flower color: Upper petal surface is red RHS 47A to RHS 46C; lower petal surface is red RHS 52B to RHS 46D.
Floret form: Salverform; sessile on spikes.
Floret (limb) diameter: Approximately 20.3 mm.
Corolla tube length: Approximately 20 mm.
Number florets per spike: 25–40 (closed to fully open florets).
Number of petals: Gamopetalous, five lobed.
Petal size:
*Length of one lobe.*—10 mm.
*Width of one lobe.*—8 mm.
Petal lobe shape: Obcordate.
Petal apex shape: Deeply emarginate.
Petal base shape: Fused.
Petal margin: Entire.
Petal texture: Smooth with fine pubescence.
Sepals: Five sepals whose margins are fused to each other along their length with a transparent membrane of less than 1 mm in width with one smaller sepal (5 mm) attached to the base of the calyx.
Calyx length: Approximately 14 mm.
Calyx width: Approximately 5 mm.
Calyx shape: Linear.
Calyx apex: Acute.
Calyx color: Yellow-green RHS 137C.
Lastingness of individual blooms: One week.
Fragrance: None.

THE REPRODUCTIVE ORGANS

Stamens: Anthers and filaments fused to upper half of corolla tube; four anthers with two pollen sacs per anther.
Pollen amount and color: Moderate, yellow RHS 5B.
Pistil: One style approximately 18 mm; transparent to yellow RHS 1C throughout length with yellow-green RHS 144C near tip, slightly curved at the tip with one stigma yellow-green RHS 144A.
Fruit seed set: Does not freely set seed but can produce 4 narrow nutlets, approximately 4 mm long; colored grey-brown RHS 199D and enclosed in the dried calyx.

DISEASE AND INSECT RESISTANCE

Tolerant to mildew.

COMPARISON WITH KNOWN CULTIVARS

When the instant plant is compared to 'Temari Scarlet' (PPAF) the 'Lan Scarl' stems are less pubescent than 'Temari Scarlet'. 'Lan Scarl' has leaves that are shorter in length; narrower in width; and darker green than 'Temari Scarlet'. The flower color of 'Lan Scarl' is a lighter shade of orange-scarlet as compared to brighter red for 'Temari Scarlet'. 'Lan Scarl' has no petal markings while 'Temari Scarlet' has a white "eye" at the base of the petals.

COMPARISON WITH PARENTAL CULTIVARS

When 'Lan Scarl' is compared to the female parent, 97-428-6, 'Lan Scarl' has a scarlet colored flower versus a red flower for 97-428-6. 'Lan Scarl' has a more trailing growth than 97-428-6 and 'Lan Scarl' is more mildew tolerant than 97-428-6. When compred to the male parent 'Temari red', 'Lan Scarl' has a lighter colored scarlet than 'Temari red'. 'Lan Scarl' has more vegetative growth in the center of the plant than 'Temari red' and 'Lan Scarl' is earlier to flower than 'Temari red'.

I claim:

1. A verbena plant as shown and described herein.

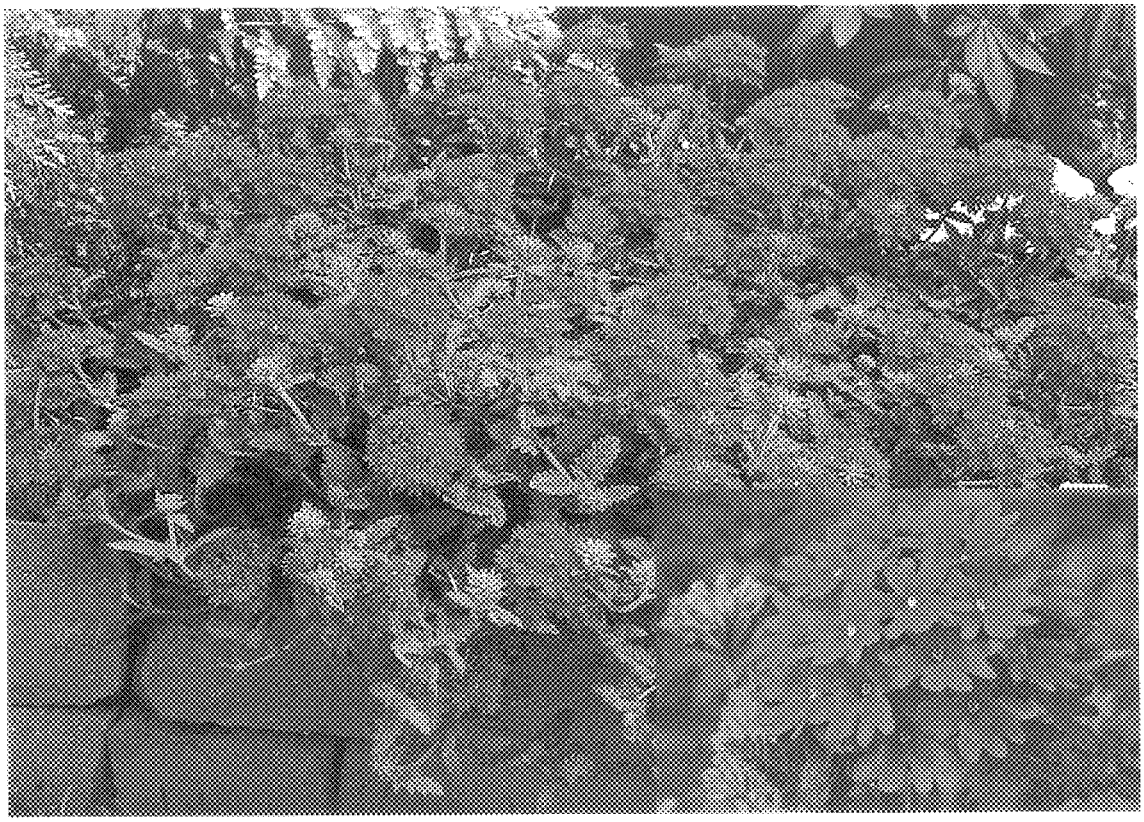

* * * * *